United States Patent [19]

Pomato et al.

[11] Patent Number: 5,578,289
[45] Date of Patent: Nov. 26, 1996

[54] IN VIVO BINDING PAIR PRETARGETING

[75] Inventors: Nicholas Pomato, Frederick, Md.;
Richard P. McCabe, West Chester, Pa.;
Gregory A. Hawkins, Hastings, Nebr.;
Reinhard Bredehorst, Hamburg,
Germany; Chong-Ho Kim, Rockville,
Md.; Carl-Wilhelm E. Vogel,
Hamburg, Germany

[73] Assignee: Akzo N.V., Arnhem, Netherlands

[21] Appl. No.: 140,186

[22] PCT Filed: Mar. 3, 1993

[86] PCT No.: PCT/US93/01858

§ 371 Date: Nov. 4, 1993

§ 102(e) Date: Nov. 4, 1993

[87] PCT Pub. No.: WO93/17707

PCT Pub. Date: Sep. 16, 1993

Related U.S. Application Data

[63] Continuation-in-part of Ser. No. 846,453, Mar. 4, 1992, abandoned.

[51] Int. Cl.$^6$ .................. A61K 39/395; A61K 51/00; A61K 51/10
[52] U.S. Cl. .................. 424/1.53; 424/1.57; 424/178.1; 424/179.1; 424/181.1; 424/183.1
[58] Field of Search .................. 424/1.1, 9, 85.91, 424/1.57, 1.77, 1.65, 181.1, 183.1, 1.53, 178.1, 179.1; 435/188; 530/391.5, 391.9

[56] References Cited

U.S. PATENT DOCUMENTS

| | | | |
|---|---|---|---|
| 4,002,532 | 1/1977 | Weltman et al. | 424/12 |
| 4,468,469 | 8/1984 | Atkinson et al. | 436/500 |
| 4,661,347 | 4/1987 | Muller-Eberhard et al. | 424/85 |
| 4,762,707 | 8/1988 | Jansen et al. | 424/85 |
| 4,975,278 | 12/1990 | Senter et al. | 424/94.3 |

FOREIGN PATENT DOCUMENTS

| | | |
|---|---|---|
| 2005162 | 6/1991 | Canada . |
| 2384262 | 10/1978 | France . |
| 1595101 | 8/1981 | United Kingdom . |
| WO91/08770 | 6/1991 | WIPO . |

OTHER PUBLICATIONS

M. Pimm et al., Brit. J. of Cancer, vol. 61, pp. 508–513 (1990).

A. Broom, J. Med. Chem., vol. 32, pp. 2–7 (1989).

J. Appleman et al., J. Biol. Chem., vol. 263, No. 21, pp. 10304–10313 (1988).

T. J. McCallister et al., FASEB Journal 2, vol. 4, p. A690, Abstract No. 2284, Mar. 1988.

R. Rando, Methods in Enzymology, vol. 46, pp. 28–41 (1977).

J. Inglese et al., J. Med. Chem., vol. 32, pp. 937–940 (1989).

R. Silverman et al., Medicinal Research Reviews, vol. 4, No. 3, pp. 415–447 (1984).

H. Nygren et al., J. Immunol. Methods, vol. 85, pp. 87–95 (1985).

F. Lee et al., Biochemistry, vol. 28, pp. 225–230 (1989).

P. Blackburn et al., "Pancreatic Ribonuclease", The Enzymes, vol. XV, pp. 317–433 (1982).

B. Birdsall et al., "Dihydrofolate Reductase: Multiple Conformations and Alternative Modes of Substrate Binding," Biochemistry, vol. 28, 1989, pp. 2297–2305, Easton, PA, USA.

Primary Examiner—Mary E. Ceperley
Attorney, Agent, or Firm—William M. Blackstone; Mary E. Gormley

[57] ABSTRACT

A method for in-vivo targeting a functional moiety in a patient by administering a targeting moiety coupled to an affinity component, wherein the targeting moiety has affinity for binding sites in a target area, and administering a binding partner to the affinity component coupled to a functional moiety to localize the functional moiety in the target area. Preferably the targeting moiety is an antibody and the functional moiety is a radiometal when performing in vivo imaging or therapy. The affinity component may be a novel methotrexate analog.

11 Claims, 13 Drawing Sheets

EFFECTS OF TREATING rhDHFR
WITH SULFO-LC-SPDP

| MOLAR RATIO DHFR:LC-SPDP | NUMBER SPDP INCORPORATED | % ACTIVITY REMAINING |
|---|---|---|
| 1:50 | 4 | 0 |
| 1:25 | 2 | 1.7 |
| 1:15 | 1.5 | 21 |
| 1:7 | 1 | 55 |

FIG.2

EFFECTS OF TREATMENTS OF rhDHFR

| TREATMENT | % RECOVERY | REMAINING SP. ACTIVITY |
|---|---|---|
| NONE | ---- | 20 U/mg |
| 7 MOLAR EXCESS SULFO-LC-SPDP | 69.6 | 11 U/mg |
| 10 mM DTT AFTER SULFO-LC-SPDP | 38.0 | 16.5 U/mg |

FIG.3

NUMBER OF ACTIVE rhDHFR

| CONJUGATE | # hDHFR/IgM |
|---|---|
| CON5-12 | <<1 |
| CON10-25 | <<1 |
| CON-LS2.1 | <<1 |
| 16-88DHFR3-1 | 3 |
| 16-88DHFR3-2 | 2-3 |
| 16-88DHFR3-3 | 2-3 |

FIG.5

IN VIVO BINDING PAIR PRETARGETING

This application is the National Phase of PCT/US93/01858, filed Mar. 3, 1993, and published as WO93/17707 Sep. 16, 1993 which is a continuation-in-part of U.S. Ser. No. 07/846,453, filed Mar. 4, 1992, now abandoned.

BACKGROUND OF THE INVENTION

Currently, a broad spectrum of diagnostic and therapeutic agents is used for in vivo diagnosis and treatment of cancer and infectious diseases. Radionuclides, one important group of pharmaceutical agents, have been shown to be useful for radioimaging and radiotherapy. Radioimaging compounds include metal chelates of radioisotopes such as $^{111}$In, $^{67}$Ga, $^{99m}$Tc, or $^{57}$Co, which are used to detect cancer lesions by intravenous administration. Radiotherapeutic agents, such as metal chelates of $^{90}$Y, exert their cytotoxic effects by localized cell destruction via ionizing radiation. Radionuclides, however, suffer from a number of limitations. A particular problem is caused by their toxic side effects, which limit the dosage that may be used safely. In certain cases, adverse side effects are so severe that an effective therapeutic dose cannot be safely administered. Therefore, specific targeting of radionuclides to internal target sites, such as solid tumors, has become a major focus of current medical research. The objective of radionuclide targeting is to improve tumor to normal tissue ratios by concentrating the radioisotope at the target site, while minimizing its uptake in non-target tissues.

Monoclonal antibodies, reactive with human tumor-associated antigens, provide promising agents for the selective delivery of radionuclides. Various methods have been described for the conjugation of radionuclides to antibodies. In one procedure, the tyrosine residues of the antibody molecule are labeled with $^{131}$I. Alternatively, bifunctional chelating agents are applied to bind radioisotopes to antibodies. The bifunctional chelating agents contain as one functional group a chelating moiety capable of forming a tight complex with a metal ion, and as a second functional group a chemically reactive moiety, such as an activated ester, a nitro or amine group, through which the compounds can be coupled to the antibody. Since bifunctional chelator molecules have been shown to increase the stability of isotope antibody conjugates, the latter labeling procedure has gained favor in clinical trials. Despite some promising results, the data from these studies demonstrate that the use of radioisotope antibody conjugates has several limitations. The most important limitation is the high nonspecific uptake of the conjugates in normal tissues, such as liver, bone marrow, and kidney, leading to serious toxic side effects. As a result, some investigators have resorted to local or regional injections of radioisotope antibody conjugates in the area of known lesions, neglecting delivery to remote metastatic sites. Others have used antibody fragments as delivery agents, which have a lower molecular weight and, therefore, may penetrate deeper into tumors. However, they also exhibit high uptake in certain normal tissues resulting in a low therapeutic index.

A recent approach to overcoming these problems has been the development of bifunctional monoclonal antibodies. Such antibodies have a dual specificity, with one binding site for a disease site, e.g. a tumor target, and one binding site for a hapten, which can function as a carrier for a variety of diagnostic and therapeutic agents including radionuclides. The dual specificity allowed the development of a two step targeting procedure for radionuclides. First, the anti-hapten, anti-tumor bifunctional antibody is administered and, after a period of time sufficient for the bifunctional antibody to localize at the tumor site, the radionuclide-derivatized hapten is injected. This approach has the advantage that the non-toxic targeting moiety and the toxic radionuclide-derivatized hapten can be given separately. As a result, large quantities of the targeting moiety can be administered without the risk of serious toxic side effects. Furthermore, increased uptake ratios and faster localization of the radionuclide can be expected, since the radioactivity is attached to the low molecular weight structure of the radionuclide-derivatized hapten capable of fast distribution through the body tissues and rapid clearance through the kidneys.

The bifunctional antibody approach, however, suffers from the fact that the antibody molecule is composed of two monovalent antibody fragments with different specificities. The avidity of monovalent antibody fragments such as Fab fragments is orders of magnitude lower than that of bivalent antibody molecules. The efficacy of the two step bifunctional antibody approach, however, is dependent on high avidity binding of the bifunctional antibody to the radionuclide-derivatized hapten and to extracellular or cell surface antigens at the target site. Moreover, to allow for efficient clearance of non-bound bifunctional antibody from circulation before injection of the radionuclide-derivatized hapten, a period of 4 to 6 days is required. Using monovalent antibody fragments, complete dissociation of bound antibody molecules from the target sites is expected in this period of time. A recent study of the kinetics of antibody binding to surface-immobilized antigen demonstrated that the intact antibody, bound to the surface-immobilized antigen, did not dissociate significantly over a period of almost 3 days, whereas a monovalent Fab' fragment prepared from the same antibody dissociated from the surface-bound antigen with a half-life of 16 hours (N. Nygren, C. Czerkinsky, M. Stenberg, Dissociation of antibody bound to surface-immobilized antigen. J. Immunol. Meth. 85, 87–95, 1985).

In addition to the limitation of monovalent binding, there are problems with the current procedures for the production of bifunctional antibodies. In one method two Fab' fragments of differing specificity are chemically linked to form a F(ab)$_2$ fragment with dual specificity. The preparation of appropriate antibody fragments requires individual adjustment of the experimental conditions for each monoclonal antibody, the yields are often very low, and the hybrid antibodies usually suffer significant, irreversible denaturation. Such denaturation can reduce immunoreactivity and would be expected to result in different metabolic characteristics in vivo. Alternatively, fusion of two hybridomas or a hybridoma with immune spleen cells can be undertaken, with appropriate physical or biochemical selection of hybrid hybridomas. The theoretical maximum yield of bifunctional antibody, produced by established hybrid hybridomas, will be 50% of the total immunoglobulin synthesized, the remainder being bivalent parent antibodies. However, the actual production of bifunctional antibody can be much lower. In a recent study a bispecific monoclonal antibody against methotrexate and a human tumor associated antigen was prepared to augment the cytotoxicity of a methotrexate-carrier conjugate. (M. V. Pimm, R. A. Robins, M. J. Embleton, E. Jacobs, A. J. Markham, A. Charleston and R. W. Baldwin, Br. J. Cancer, vol.61, pp.508–513, 1990). The proportions of the total immunoglobulin recovered from the hybrid hybridoma were 60% monospecific antibody from the original hybridoma cells, 27% monospecific antibody from the immune spleen cells, and only 13% bispecific antibody, suggesting a preferential association of homologous heavy chains. These data demonstrate that it will always be necessary when using the hybrid-hybridoma technique to develop strategies for purification of the bifunctional antibody from parent antibodies being produced by the hybridoma. Since the different antibody molecules from one hybrid hybridoma share most properties, an efficient removal of the monospecific antibodies would require two affinity purification steps, a time consuming procedure known to cause partial denaturation of the purified antibodies.

The problems listed in the foregoing are not intended to be exhaustive, but rather to describe many of the factors that tend to limit the potential clinical value of the described agents. While the two-step procedure, developed for bifunctional antibodies, provides some advantages over other targeting procedures, there exists a need for a more effective means by which the concentration of a radionuclide or another diagnostic or therapeutic agent may be maintained at in vivo target sites for a period of time sufficient to achieve desired results. Further, there exists a need for an effective delivery system consisting of components that can be easily synthesized and purified at high yields.

SUMMARY OF THE INVENTION

One general object of the invention is to provide a delivery system for targeting therapeutic or diagnostic compound to an in vivo target, which substantially overcomes the limitations known in the prior art. A more specific objective of the invention is to provide methods and components for selectively targeting radionuclides to solid tumor areas.

This invention comprises a system for in vivo localization using a non-toxic targeting moiety coupled to a non-toxic enzyme, which will localize to a target site, and an enzyme inhibitor or enzyme substrate derivatized with a functional moiety. On administration, the derivatized enzyme inhibitor or substrate binds to the localized non-toxic enzyme coupled to the targeting moiety, presenting the functional moiety to the tissue at the target site. In the preferred embodiment the targeting moiety is an antibody or antibody fragment and the functional moiety bound to the enzyme inhibitor is a radionuclide. According to the invention the targeting moiety and enzyme are both non-toxic and minimally or non-immunogenic when coupled, and the derivatized enzyme inhibitor or substrate is also preferably weakly or poorly immunogenic and non-toxic. A further requirement for the enzyme coupled to the targeting moiety is that it be essentially absent from circulation or present in only very low quantities in circulation. With this invention there is rapid and specific localization of the targeting moiety coupled to the enzyme, and relatively rapid clearance and specific targeting of the functional moiety-derivatized enzyme inhibitor or substrate with extremely little non-specific binding. By these means highly toxic or otherwise undesirable functional moieties can be used in therapy and in imaging. This invention also comprises a novel methotrexate analog useful for making the functional moiety derivitized enzyme inhibitor and a stabilized dihydrofolate reductase enzyme.

BRIEF DESCRIPTION OF THE DRAWINGS

FIG. 2 shows the effects of incorporation of a spacer with a terminal sulfhydryl group through amino groups on dihydrofolate reductase using SPDP. Sulfhydryl incorporation and protein concentration determination were performed as described for the antibody.

The activity of rhDHFR following sulfo-LC-SPDP modification and following reduction with DTT was evaluated to determine the effects of the treatment on the activity of the enzyme, shown in FIG. 3.

Figure 4:
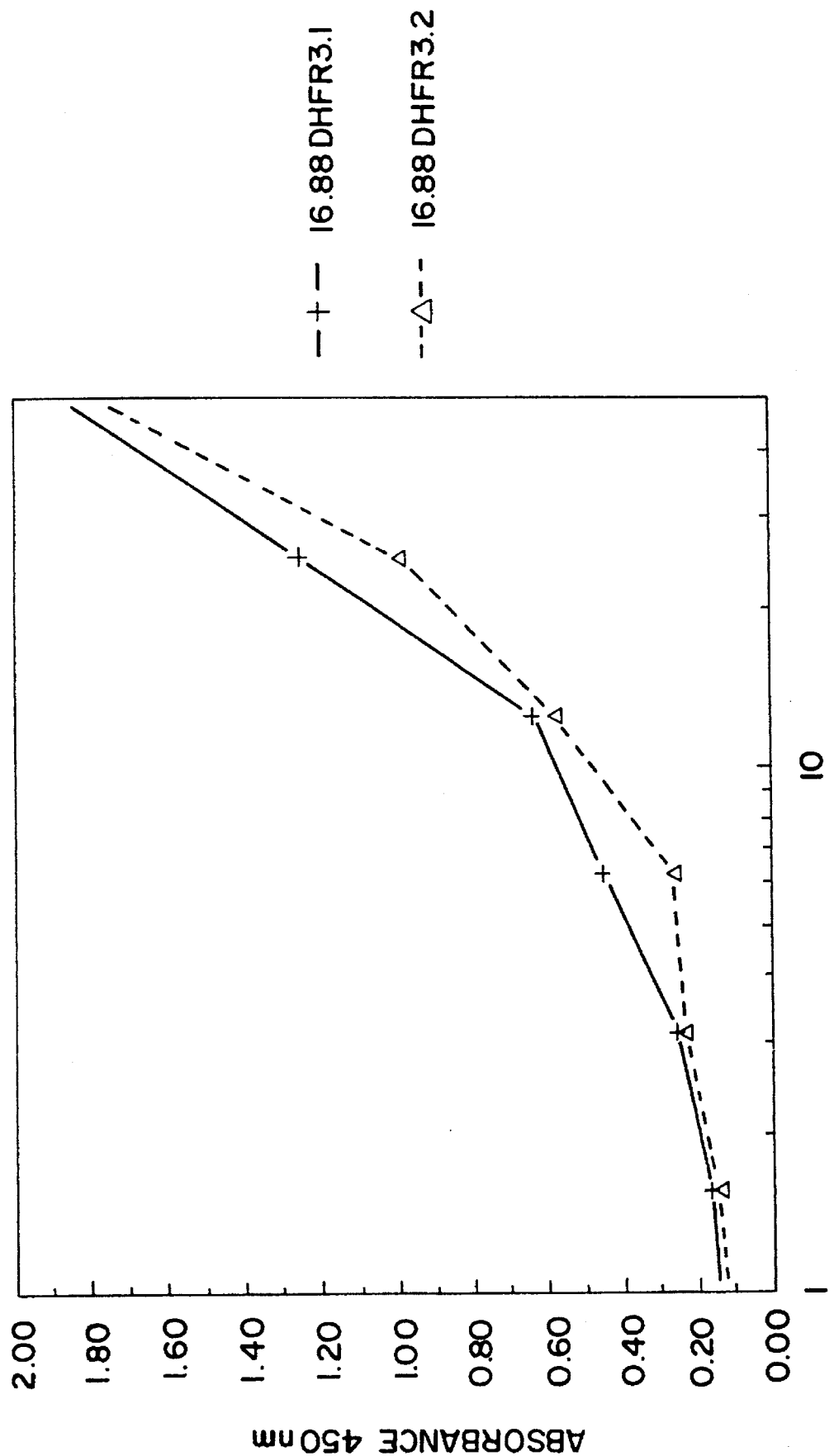

FIG. 4 shows the immunoreactivity of two preparations of 16.88-DHFR.

FIGS. 5 shows the number of active rhDHFR molecules per IgM molecule and shows the beneficial effects of using the LC-SPDP spacer compared to normal SPDP in three different conjugate preparations.

Figure 6:
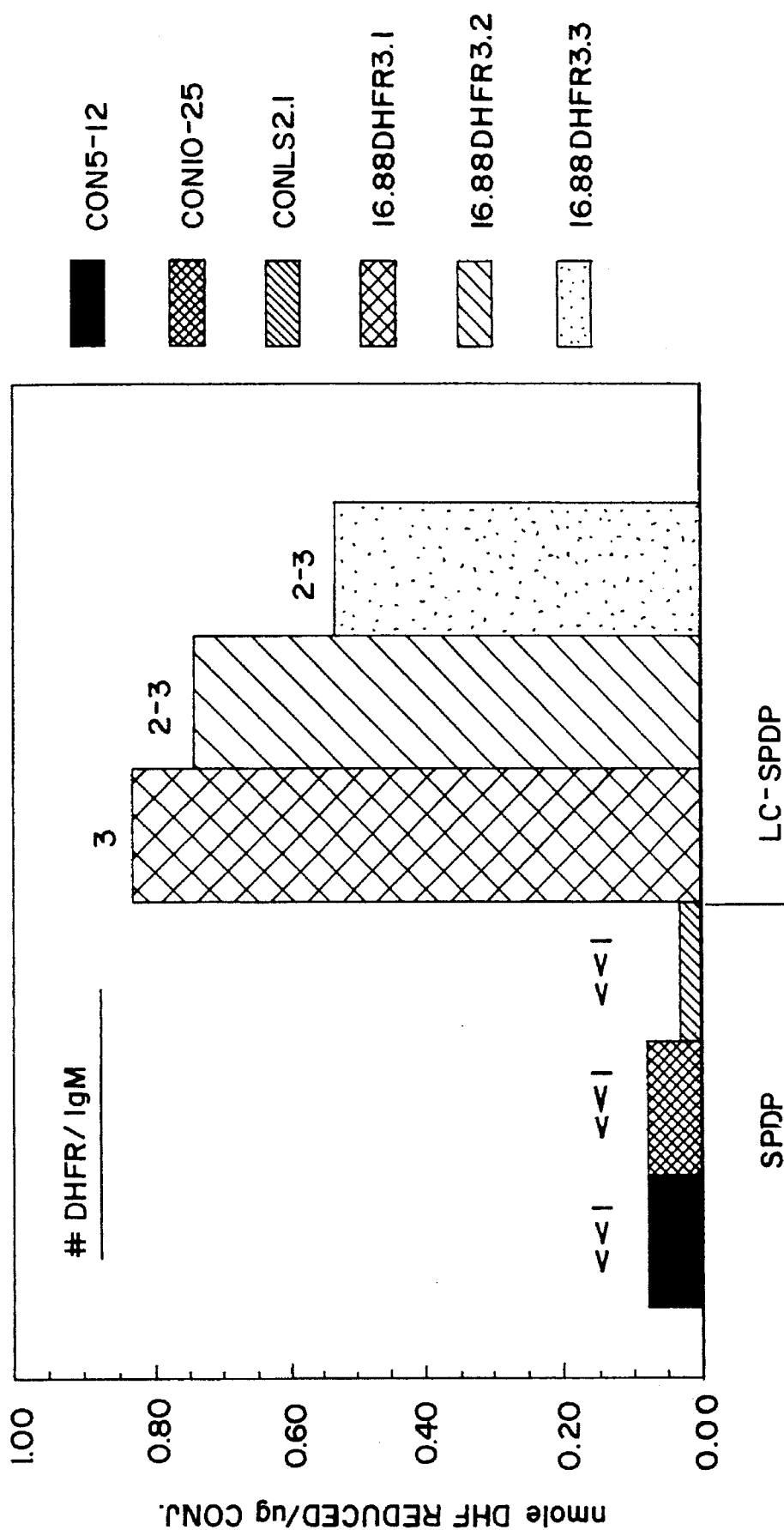

FIG. 6 shows the activities of 16.88-DHFR conjugates prepared with LC-SPDP and SPDP alone. Benefits are seen with the LC-SPDP spacer.

Figure 7:
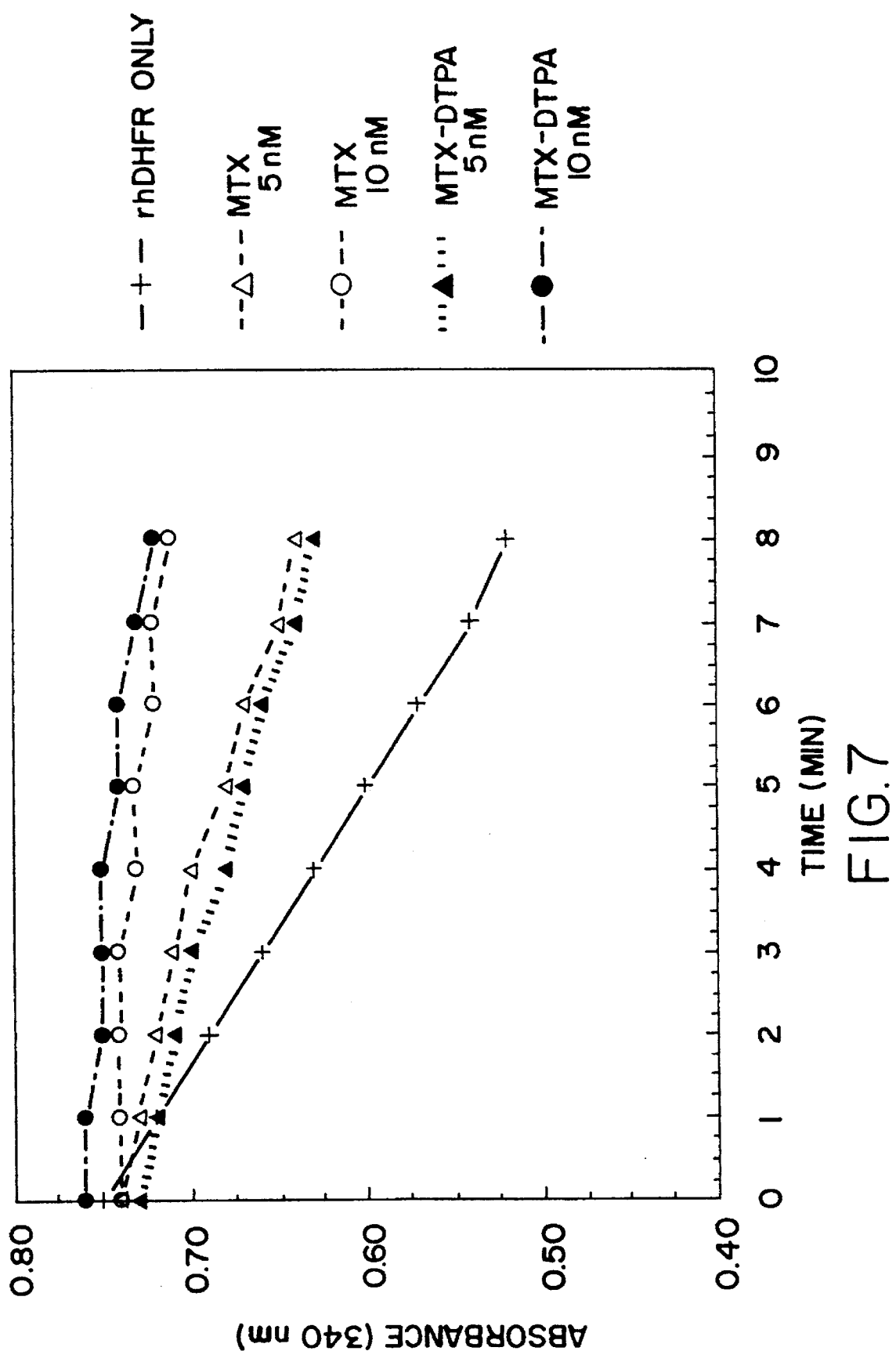

FIG. 7 shows the inhibition of rhDHFR by MTX vs. MTX-DHFR, wherein the concentration of rhDHFR is 10 nM. At $1 \times 10^{-8}$M and $5 \times 10^{-9}$M inhibitor concentration, the inhibitory effects of DTPA-MTX were virtually identical to MTX inhibition, as indicated by the decreased rates of dihydrofolate reduction.

Figure 8:
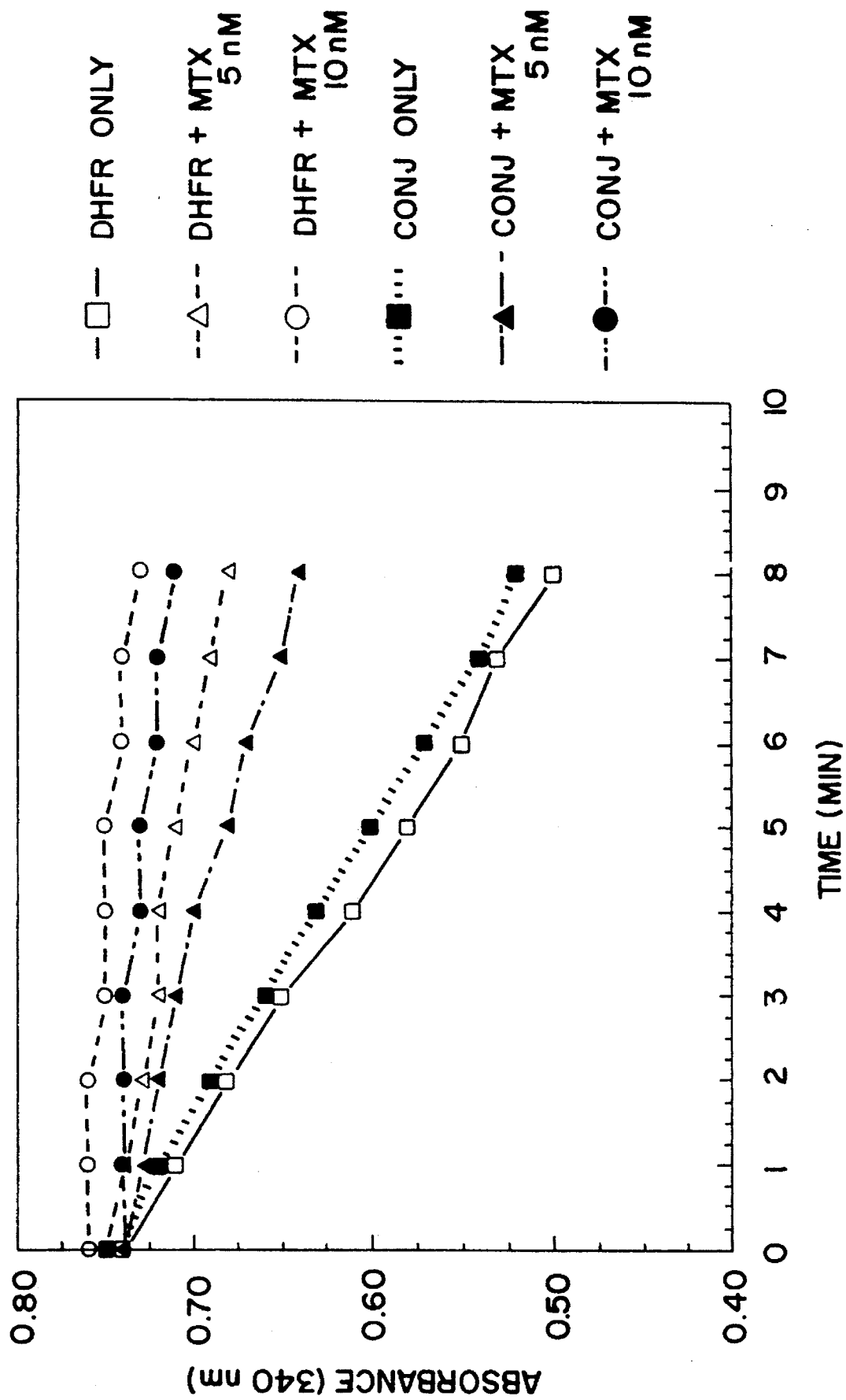

FIG. 8 shows the results of MTX inhibition of equivalent activities of native rhDHFR and 16.88 bound rhDHFR and indicates that MTX binding is proportional to the reductase activities regardless of whether it is free or in conjugate form. See Example VI.

Figure 9:
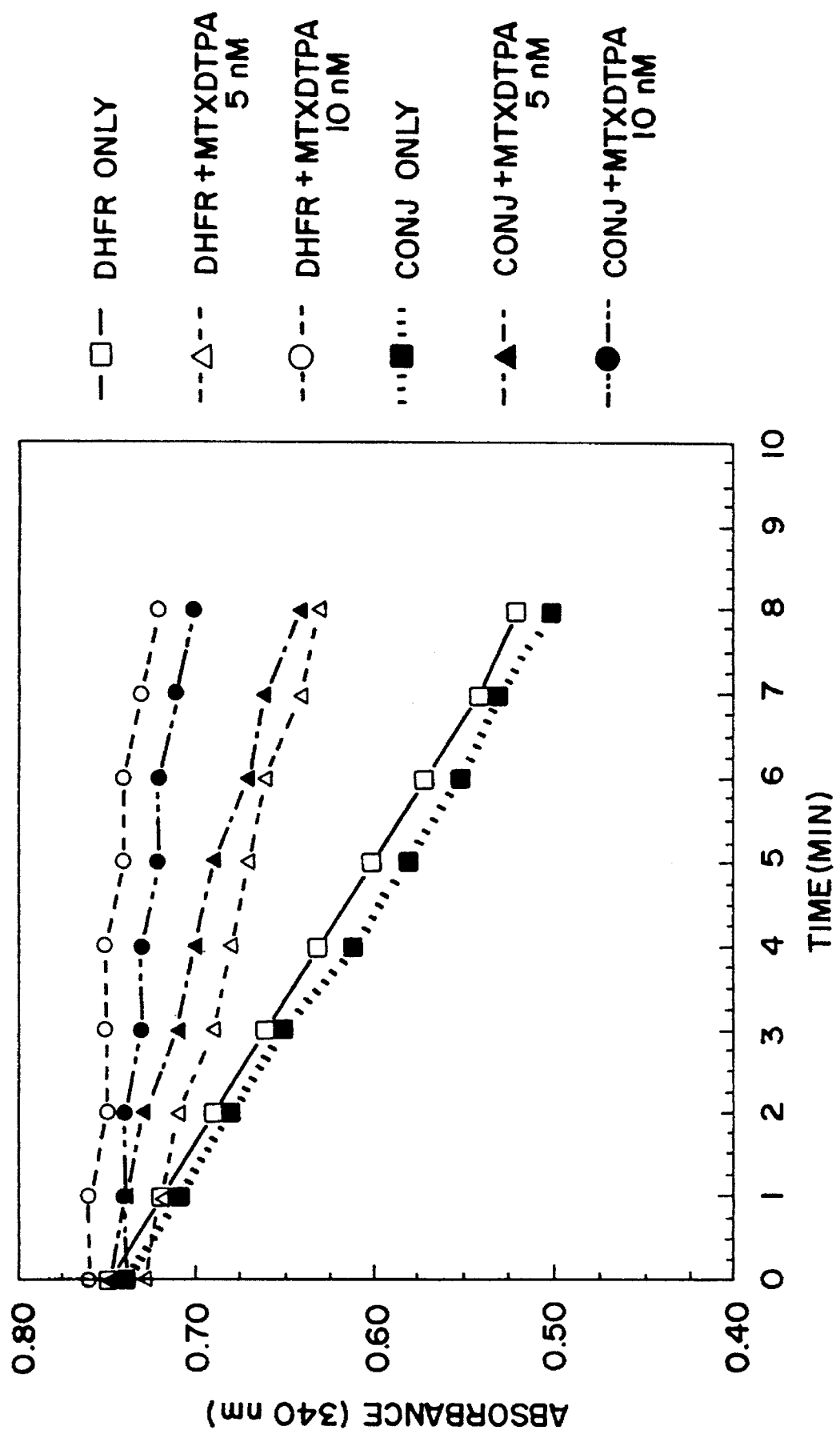

An identical experiment as that shown in FIG. 8 performed using DTPA-MTX (FIG. 9) confirmed the methotrexate data. See Example VI.

Figure 10:
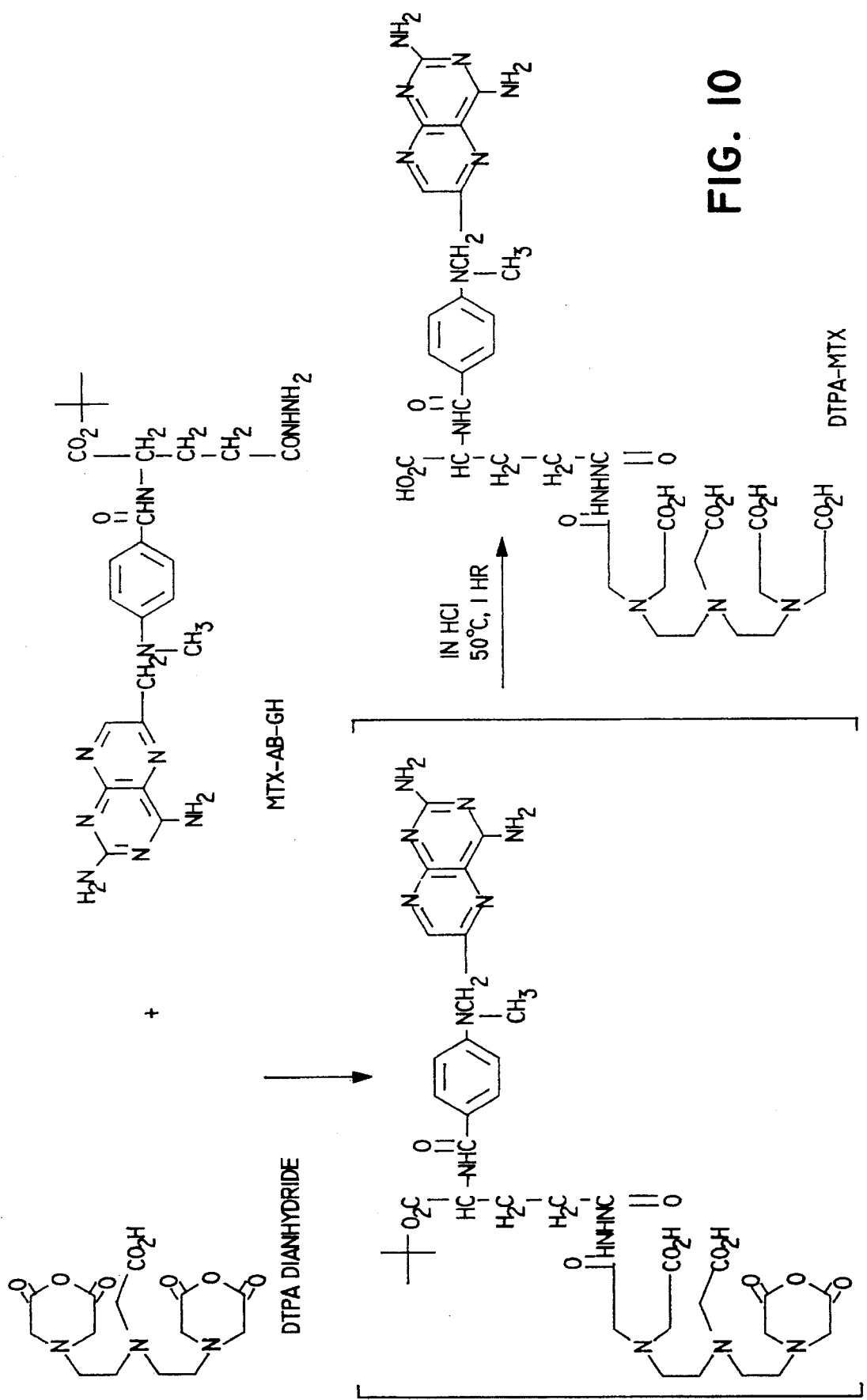

The synthesis of DTPA-MTX is shown schematically in FIG. 10.

Figure 11:
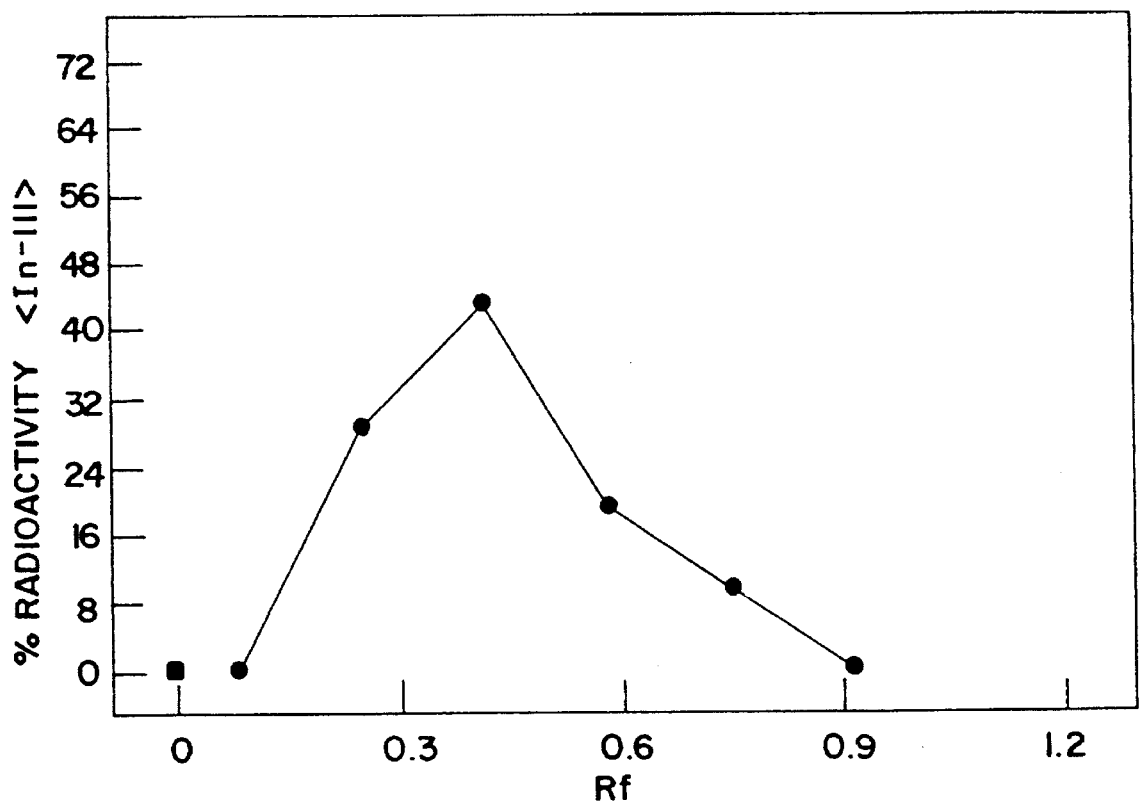

FIG. 11 is a TLC radiochromatograph which shows the migration of $^{111}$In-DTPA-MTX in the silica gel with an $R_f$ of 0.5 to 0.7. Free $^{111}$In does not migrate from the origin in this system.

Figure 12:
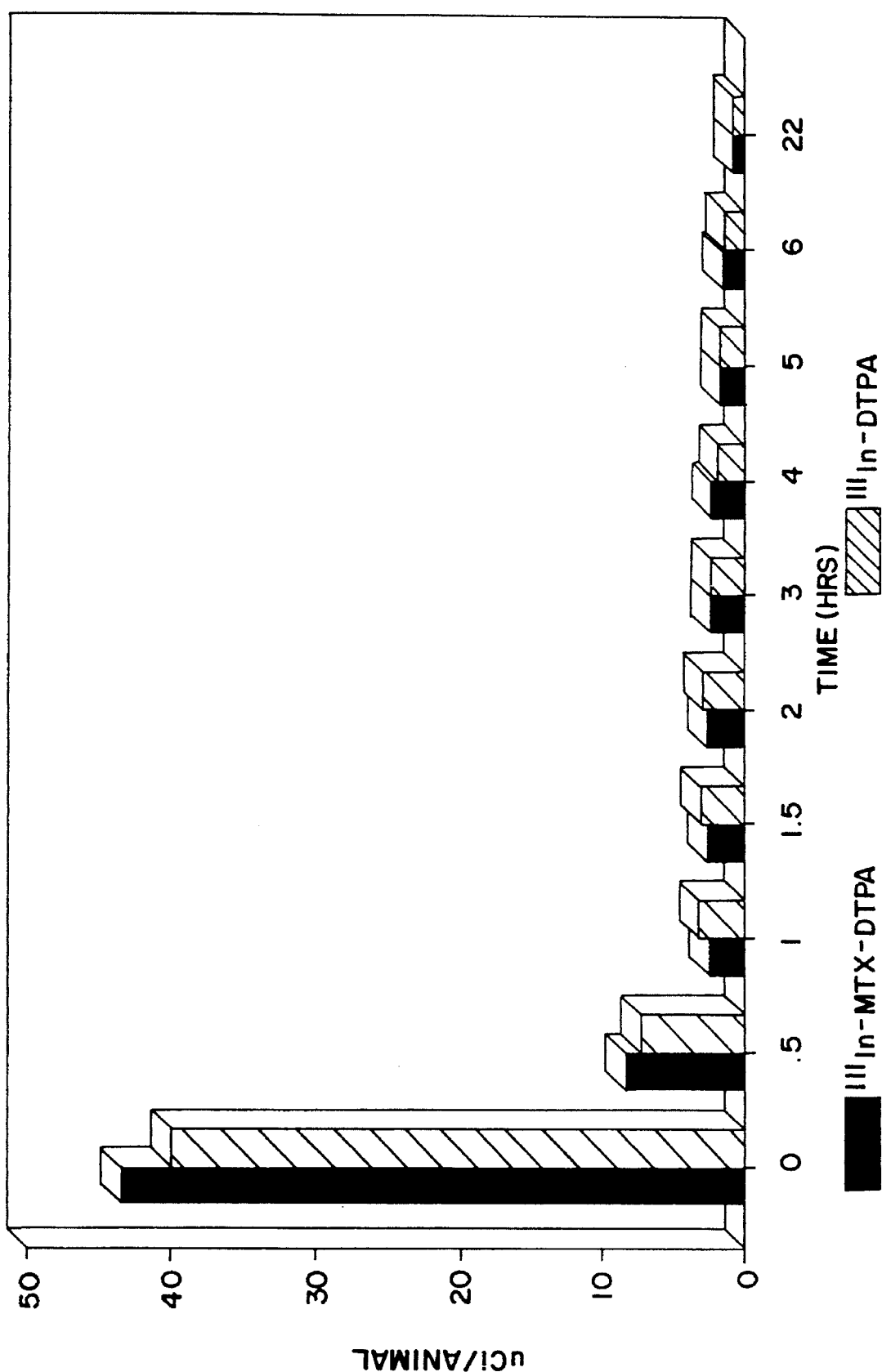

FIG. 12 is a bar graph showing clearance of $^{111}$In-DTPA-MTX and that the $^{111}$In-DTPA-MTX and the $^{111}$In-DTPA clear from the mice at similar rates indicating the likelihood of rapid urinary excretion of a DTPA-MTX not bound to antibody-DHFR.

Figure 13:
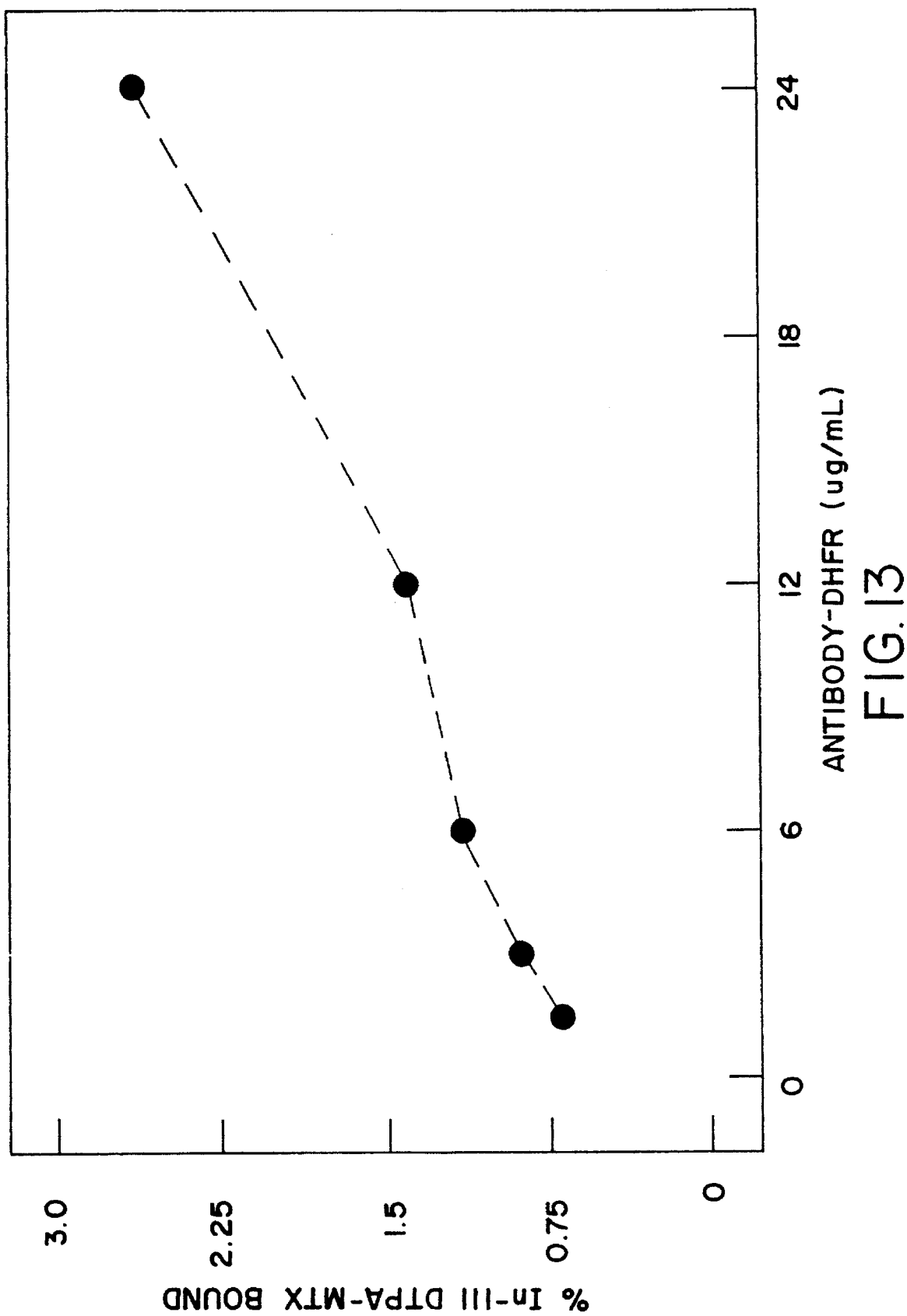

FIG. 13 shows the results of $^{111}$In-DTPA-MTX binding to antibody-DHFR bound to tumor cells at different concentrations. See Example IX.

Figure 14:
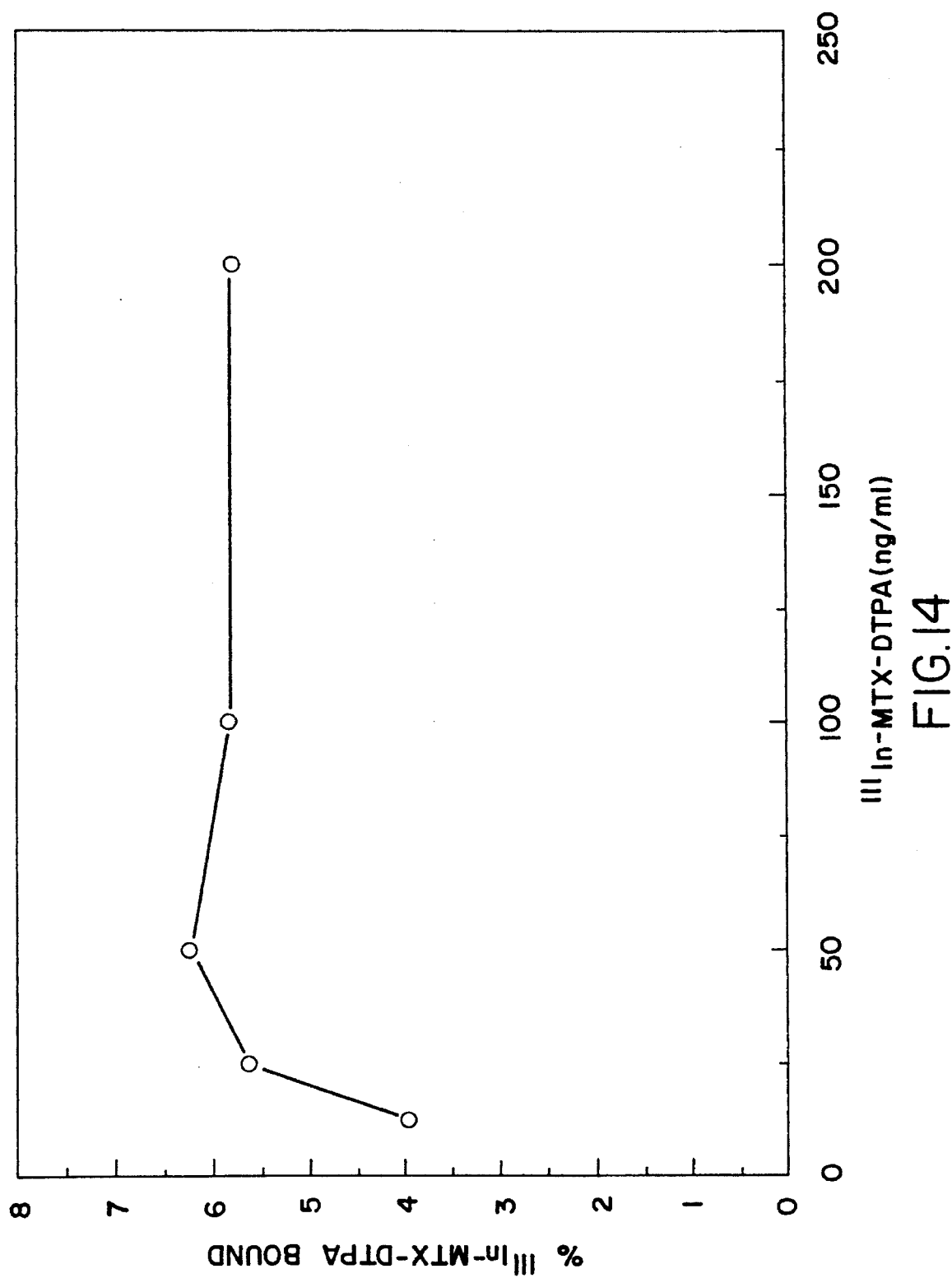

FIG. 14 shows the results of $^{111}$In-DTPA-MTX binding to antibody-DHFR bound to tumor cells, using different concentrations of $^{111}$In-DTPA-MTX. See Example IX.

DESCRIPTION OF THE PREFERRED EMBODIMENTS

Preferred methods for localizing radionuclides at an internal target site in a patient include two, three, four and five step procedures. The three, four and five step embodiments are refinements of the basic concept.

First, a non-toxic targeting moiety coupled to a non-toxic enzyme is administered parenterally to a patient and allowed to localize selectively at the target site. Non-localized circulating molecules of the targeting moiety-enzyme conjugate are allowed to clear from the circulatory system. If necessary, this clearing can be accelerated in vivo by complex formation or ex vivo by adsorption to a specific matrix using binding partners, such as antiidiotypic antibodies or antigens, (second step of the three-step procedure). Thereafter, a radionuclide-derivatized enzyme inhibitor or substrate, specific for the enzyme conjugated to the targeting moiety, is given parenterally. Binding of radiolabeled enzyme inhibitor or substrate to the localized enzyme-derivatized targeting moiety and rapid clearance of unbound radiolabeled enzyme inhibitor results in selective localization of the radionuclide at the target site.

Additional refinements include scavenging of unbound radionuclides using chelators as an additional step after administering the radionuclide conjugate. An additional step is also the administration of a blocking agent for enzyme inhibitor or substrate binding sites on cells, so the conjugate will only bind to the previously administered enzyme. Combinations of these procedures are contemplated within the invention.

The targeting moiety is preferably an antibody, an antibody fragment, an antibody variable region, a complimentarily determining region of an antibody, a bivalent antibody, a hybrid antibody or a chimeric antibody. The targeting moiety is typically an antibody reactive with a human tumor associated antigen. Particularly preferred for use in the invention are bivalent or multivalent human or chimeric monoclonal antibodies that bind with high avidity to tumor associated antigens located in an extracellular area (e.g. necrotic area) or on the cell surface and are not internalized upon binding to a cell surface antigen. The enzyme moiety preferred for use in the invention is of human origin or human-like, either by being genetically conserved or by being from a genetically similar species. An important requirement of the invention is that the enzyme used in the immunoconjugate must be essentially absent or present in only very low quantities in the circulation, extracellular areas, or on the cell surface of target organs to avoid blocking enzyme inhibitor or non-specific binding. In one embodiment, the enzyme is human dihydrofolate reductase, a single chain molecule of human origin that does not occur in extracellular fluids in measurable quantities. The third component of the targeting system is a radionuclide-derivatized enzyme inhibitor capable of binding with high affinity to the antibody-conjugated enzyme. Preferred for use in the invention are small molecular weight inhibitors that allow fast distribution through the body tissues and quick clearance by excretion of unbound inhibitor. The term enzyme inhibitor used in this invention encompasses molecules that bind to the enzyme and may augment, reduce, or leave unchanged enzymatic activity. Furthermore, the inhibitor molecule should be suitable for derivatization with radionuclides, e.g., by covalent attachment of a chelator molecule complexed with a radioactive metal, without impairing its affinity for the enzyme. In the preferred embodiment the radionuclide-derivatized enzyme inhibitor is a conjugate of methotrexate, a potent inhibitor of human dihydrofolate reductase, and diethylenetriaminepentaacetic (DTPA) acid complexed with $^{111}$In or $^{90}$Y. Using the gamma-carboxyl residue of methotrexate for conjugation to the chelator, the affinity of the inhibitor to dihydrofolate reductase is not affected.

Those skilled in the art will recognize that the present invention is not limited to the targeting of radionuclides. A variety of diagnostic and therapeutic agents other than radionuclides may be attached to the enzyme inhibitor. Furthermore, two or more diagnostic or therapeutic agent residues may be attached to the inhibitor, for example via an oligomeric or polymeric carrier that is modified by one or more agent residues. Oligomeric or polymeric carriers useful in this regard include natural and synthetic molecules such as polypeptides and oligosaccharides. Those skilled in the art will further recognize that the invention permits the introduction of additional residues to change the pharmacokinetic properties of the methotrexate-agent conjugates. For example, hydrophilic residues, such as sulfate or sulfonate groups, may be covalently attached to the conjugates to minimize non-specific binding to non-target proteins in serum or on cell surfaces, and to prevent cellular uptake in non-target tissues.

Another important requirement of the invention is that the system components must be non-immunogenic or poorly immunogenic. In the case of treating humans, the targeting moiety, e.g., an antibody, and the enzyme should be of human origin, humanized, or human-like, either by being genetically conserved or by being from a genetically similar species. Alternatively, components having masked immunogenic epitopes and, therefore, of poor immunogenicity may be used. Also, the radionuclide-derivatized enzyme inhibitor must be essentially non-immunogenic. The development of human antibodies against foreign proteins has been demonstrated in many studies. Human anti-mouse antibody formation in cancer patients has been reported after single injections of murine monoclonal antibodies. Human anti-mouse antibody (HAMA) formation occurs in up to 50% of cancer patients following single injections of murine monoclonal antibodies, (T. J. McCallister. S. E. Halpern, R. O. Dillman, D. L. Shawler, FASEB J. 2, 690, 1988), thereby limiting the applicability of these agents to a period of time required for the development of antibodies.

The targeting system described in this invention provides an affinity system that eliminates the serious limitations of currently available targeting techniques. Most importantly, all system components are high affinity components. The use of bivalent (e.g. IgG antibodies) or multivalent (e.g. IgA or IgM antibodies) agents as targeting moieties results in efficient natural clearance of non-bound antibody-enzyme conjugates over a period of several days without risk of complete dissociation of bound conjugates from the target sites. The use of enzyme inhibitors and the corresponding enzymes in an affinity system offers several advantages. First, some enzyme inhibitors are known to bind with extremely high affinities to the corresponding enzyme. For example, the overall binding constant of methotrexate to human dihydrofolate reductase ($K_{off}/K_{on}$: $2.1 \times 10^{-10}$M) is rarely matched by the affinity of anti-hapten monoclonal antibodies. Second, enzyme:enzyme inhibitor systems offer the unique possibility of further increasing affinity by constructing multisubstrate analogue inhibitors (A. D. Broom, "Rational Design of Enzyme Inhibitors: Multisubstrate Analogue Inhibitors," J. Med. Chem. 32, 2–7, 1989). Recently, a multisubstrate adduct inhibitor of a purine biosynthetic enzyme (glycinamide ribonucleotide transformylase) with a picomolar dissociation constant has been synthesized (J. Inglese, R. A. Blatchly, S. J. Benkovic, J. Med. Chem. 32, 937–940, 1989). The inhibitor contains derivatives of the two substrates of the biomolecular, enzyme-catalyzed reaction, 10-formyl tetrahydrofolate and glycinamide ribonucleotide. The binding affinity of this multisubstrate inhibitor is approximately 3-fold higher than the product of the $K_m$ values of the two substrates, and $10^3$–$10^6$ times higher than the binding affinity of either substrate. In addition to multisubstrate inhibitors, suicide or mechanism-based inhibitors can be used. These inhibitors require interaction with the target enzyme in such a way as to initiate the catalytic process. As the reaction proceeds, a latent functional group, usually an electrophile, is unmasked within the active site.

Alkylation or acylation of a suitably disposed active-site nucleophile inactivates the enzyme (R. B. Silverman, S. J. Hoffman, J. Med. Res. Rev. 4, 415, 1984). The advantage of suicide inhibitors is that upon binding of the inhibitor to the enzyme a covalent linkage between the two molecules is formed. As a result, radionuclide-derivatized inhibitor molecules bound to targeted antibody-enzyme conjugates cannot dissociate.

DETAILED DESCRIPTION OF THE INVENTION

Multi-substrate Analogues of the Inhibitor Choice of Antibody

Conventional polyclonal antibodies may be applied as carrier molecules within the concept of the invention. However, monoclonal antibodies offer multiple advantages. Each monoclonal antibody is specific for one antigenic determinant. Thus, with monoclonal antibodies the extent of non-specific binding to normal tissues and subsequent toxicity to normal non-target tissues is reduced. In addition, since unlimited amounts of each monoclonal antibody can be produced, all individual preparations of antibody can be controlled to ensure that antigen specificity remains constant over the life of the antibody product. Different monoclonal antibodies specific for different epitopes with the same tissue specifications may be combined. Thus, when using a monoclonal antibody or a mixture of monoclonal antibodies the efficacy and control of the delivery system is improved without sacrificing any contributions to the efficacy of the system that may be obtained with conventional polyclonal reagents.

A preferred approach is to use monoclonal or polyclonal antibodies of the same species of origin as the animal receiving therapy. It is not required that these antibodies be internalized by the target cell. For the most part, with the exception of veterinary applications, the use of human, humanized or chimeric antibodies that are primarily human in their construction, is most desirable. Many human monoclonal antibodies have been described. Also, approaches to humanizing antibodies developed from lymphoid cells of non-human species and methods using variable region genes from non-human antibodies genetically coupled to human antibody constant region genes have been described. The advantages of the homologous and genetically engineered antibodies are several. Unlike heterologous, e.g., murine or rat antibodies, the immune response to the homologous antibody is minimal. At most, a weak response to idiotypic determinants of the human antibody occurs and then only after multiple cycles of administration. In our clinical studies with human monoclonal antibodies we have not detected any induction of an immune response to any region of the antibody, idiotypic, allotypic or framework, even after repeated doses of up to 200 mg/week. This advantage allows use of intact whole immunoglobulin rather than more rapidly metabolized antibody fragments, allows high doses of intact whole immunoglobulin to be administered and allows the use of multiple cycles of antibody administration. In addition antibodies raised in homologous species have additional advantages, as they recognize subtle antigenic differences not recognized by heterologous antibodies or even genetically engineered human antibodies.

Antibody may be directed against any target, e.g., tumor, tissue, bacterial, fungal, viral, parasitic, mycoplasmal, histocompatibility or differentiation antigens or receptors. Antibody may be from any class, IgG, IgA, IgF or IgM, and a combination of antibodies reactive to different antigenic determinants may be used.

The targeting moiety need not be restricted to antibody but may be any substance that meets the basic requirements for a targeting moiety in this invention, as long as there is an affinity for the target tissue. Thus agents that bind specifically to certain tissue receptors such as hormones, lymphokines or certain classes of infectious agents may be used.

Construction of the Antibody-Enzyme Complex

Preparation of the immunoconjugate for our targeting system requires attachment of an enzymatic or affinity component (AC) to an antibody and forming a stable complex without compromising the activity of either component. Our strategy involves incorporation of a protected sulfhydryl onto the AC using the heterobifunctional crosslinker SPDP (n-succinimidyl-3-(2-pyridyldithio) propionate and then deprotecting the sulfhydryl for formation of a disulfide bond with another sulfhydryl on the antibody. Instead of destabilizing the antibody with reducing agents to generate free sulfhydryls, new sulfhydryls will also be incorporated onto the antibody using SPDP. In the protected form, the SPDP generated sulfhydryls on the antibody react with the free sulfhydryls incorporated onto the AC forming the required disulfide bonds. By optimizing reaction conditions, the degree of SPDP modification of each component can be controlled, thus allowing maximum incorporation of the AC onto the antibody while maintaining maximum activity of each component. SPDP reacts with primary amines and the incorporated sulfhydryl is protected by 2-pyridylthione.

If SPDP should affect the activities of either the antibody or the AC, there are a number of additional crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the protein. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

Other crosslinkers are available that can be used in different strategies for crosslinking our immunoconjugate components. TPCH(S-(2-thiopyridyl)-L-cysteine hydrazide and TPMPH ((S-(2-thiopyridyl)mercaptopropionohydrazide) react at the carbohydrate moieties of glycoproteins that have been previously oxidized by mild periodate treatment, thus forming a hydrazone bond between the hydrazide portion of the crosslinker and the periodate generated aldehydes. The placement of this crosslinker on the antibody is beneficial since the modification is site-specific and will not interfere with the antigen binding site of the antibody. TPCH and TPMPH introduce a 2-pyridylthione protected sulfhydryl group onto the antibody, which can be deprotected with DTT and then subsequently used for conjugation, such as forming disulfide bonds between components. If disulfide bonding is found unsuitable for producing stable conjugates, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. This maleimide group can subsequently react with sulfhydryls on the other component, which can be introduced by previously mentioned crosslinkers, thus forming a stable thioether bond between the components. If steric hindrance between components interferes with either component's activity, crosslinkers can be used which introduce long spacer arms between components and include derivatives of some of the previously mentioned crosslinkers (i.e., SPDP). Thus there is an abundance of suitable crosslinkers, which could be used; each of which should be selected depending on the effects it has on optimal immunoconjugate production.

For our preferred embodiment, we have chosen the recombinant human enzyme dihydrofolate reductase (rhDHFR) as our affinity component and the anti-tumor IgM human monoclonal antibody 16.88 as the targeting component. Both components are modified with the SPDP derivative Sulfo-LC-SPDP by formation of a disulfide bond between the components. Sulfo-LC-SPDP is identical in its amino reactivity as SPDP but obtains a sulfo group on the succinimidyl group, conferring water solubility on the crosslinker, thus avoiding the use of organic solvents, which may have detrimental effects on the activities of both components. Also included on sulfo-LC-SPDP is a 5-carbon spacer, which reduces steric hinderance between the components. Four most preferred embodiment we first stabilize rhDHFR by covalent conjugation with ANPAP-NADP, as illustrated in Example X.

Choice of Enzyme Inhibitor Molecules

Several considerations are important for the choice of enzyme inhibitors suitable for use in the present invention. High affinity binding of the inhibitor to the corresponding enzyme is the most important requirement. The overall binding constant ($K_{off}/K_{on}$) should be in the low nanomolar to picomolar range to guarantee tight binding of radionuclide-derivatized enzyme inhibitor molecules to targeted antibody-enzyme conjugates. Methotrexate represents one example of such an inhibitor. Methotrexate binds to human dihydrofolate reductase with an overall binding constant ($K_{off}/K_{on}$) of $2.1 \times 10^{-10}$M and competitively inhibits the enzyme with a $K_i$ value of $3.4 \times 10^{-12}$M (M. R. Appleman, N. Prendergast, T. J. Delcamp, J. H Freisheim, R. L. Blakley, "Kinetics of the Formation and Isomerization of Methotrexate Complexes of Recombinant Human Dihydrofolate Reductase", J. Biol. Chem. 263, 10304–10313m 1988).

One approach to increasing the affinity of enzyme inhibitors is the construction of multisubstrate adduct inhibitors. In principle, such inhibitors can be designed for any enzyme that binds two or more substrates simultaneously (cofactors are considered to be substrates in this context). This includes, but is not limited to, methyl-, formyl- and acetyltransferases, dehydrogenases, hydroxylases, kinases, and various other enzymes such as dihydropteroate synthase, ATP:L-methionine S-adenosyl transferase, and spermidine synthase. For example, multisubstrate adduct inhibitors for enzymes catalyzing bimolecular reactions can be synthesized by covalent conjugation of both substrates. As demonstrated in several studies, some of these substrate conjugates possess the binding stabilization of both individual substrates, in addition to the entropic advantage of reduced molecularity (see, for example, J. Inglese, R. A. Blatchly, S. J. Benkovic., "A Multisubstrate Adduct Inhibitor of a Purine Biosynthetic Enzyme with a Picomolar Dissociation Constant", J. Med. Chem. 32, 937–940, 1989). Typically, the binding affinity of potent multisubstrate adduct inhibitors is $10^3$–$10^6$ times the binding affinity of either substrate. Another approach to increasing the affinity of the inhibitor-enzyme interaction is to combine a multisubstrate adduct inhibitor with an enzyme complex consisting of two or more copies of the enzyme binding site in sufficiently close position to allow the simultaneous binding of the inhibitors coupled together.

Alternatively, suicide or mechanism-based irreversible enzyme inhibitors may be used. These inhibitors require catalytic conversion by the target enzyme. The inhibitor itself is chemically unreactive, but the product of the enzymic conversion is a highly reactive molecule. This product immediately reacts with an active-site moiety, resulting in covalent attachment of the inhibitor to the enzyme and, thereby, in irreversible inactivation of the enzyme. Due to this mechanism, the efficacy of these inhibitor molecules is determined, not only by their binding affinity, but also by their capability to serve as a substrate for the target enzyme. Enzymes that function by covalent catalysis, especially pyridoxal phosphate and flavin-linked enzymes, are preferred but not the only targets for mechanism-based irreversible inhibitors. Examples of such inhibitors are beta, gamma-unsaturated amino acids used for the irreversible inhibition of pyridoxal-linked aspartate aminotransferase, gamma-cysthathionase, and tryptophan synthetase. Other examples include 2-chloroallylamine and cis-3-chloroallylamine, irreversible inhibitors of nonflavin-linked monoamine oxidase and flavin-linked monoamine oxidase, respectively (R. R. Rando. Mechanism-based irreversible enzyme inhibitors. Meth. Enzymol. 46, 28–41, 1977).

Further important considerations for the choice of suitable enzyme inhibitors include a) minimal reactivity with normal tissues, b) low molecular weight, c) solubility in aqueous solutions, and d) the feasibility of chemical conjugation of the inhibitor to effector molecules without impairment of the binding affinity. Preferred for use in the invention are water-soluble, small molecular weight inhibitors that are capable of fast distribution through the body tissues and that can be cleared rapidly by the kidneys. In order to prevent the development of antibodies against radionuclide-derivatized enzyme inhibitor molecules, inhibitors with molecular weights less than approximately 5,000 daltons are preferred. In one embodiment of the invention, methotrexate (L-4-amino-$N^{10}$-methylpteroyl-glutamic acid), a water-soluble compound with a molecular weight of 508.5 daltons, is used as inhibitor of human dihydrofolate reductase. The gamma-carboxyl group of the glutamate moiety of this inhibitor can be derivatized without impairing its binding to the enzyme.

Although small molecular weight inhibitors are preferred, enzyme inhibitors with molecular weights larger than 5,000 daltons are also included in this invention. For example human placental ribonuclease inhibitor (PRI) is a 50 Kd protein that forms tight complexes with both secretory and intracellular ribonucleases (P. Blackburne, S. Moore. In: The Enzymes (P. D. Boyer, ed.) vol. 15, pp. 317–433, Academic Press, N.Y., 1982). As a protein with a molecular weight of 50,000 daltons PRI does not meet the desired properties of preferred inhibitors with regard to fast distribution through body tissues and rapid clearance by the kidneys. However, PRI is of human origin and competitively inhibits RNase A with an extremely low $K_i$ value of $4 \times 10^{-14}$M, approaching the affinity of avidin for biotin. Moreover, PRI binds to human angiogenin, a blood vessel-inducing protein with 35% sequence homology to pancreatic RNase, with an even lower $K_i$ value of $7 \times 10^{-16}$M (F. S. Lee, R. Shapiro, B. T. Vallee. Tight-binding inhibition of angiogenin and ribonuclease A by placental ribonuclease inhibitor. Biochemistry 28, 225–230, 1989).

Choice of Effector Molecules

Effector molecules used in the practice of the present invention are pharmacologically active agents, such as radionuclides, drugs, hormones, and anti-metabolites. They are selected according to the purpose of the intended application, such as whether for imaging or killing tumor cells. Furthermore, the selection involves the consideration of properties such as water solubility and the ease of covalent attachment to enzyme inhibitors without loss of activity.

One important class of therapeutic and diagnostic agents useful in the invention is chelated metals, including chelated radionuclides useful for tumor therapy, such as $^{186}$Re, $^{90}$Y or $^{212}$Bi, radionuclides useful for radioimaging, such as $^{99m}$Tc or $^{111}$In, chelated paramagnetic ions useful for magnetic resonance imaging, such as Gd or Mn, and radio-sensitizing chelated metals, such as chelated iron or ruthenium. Effector molecules may also include, for example, anti-tumor agents, such as DNA alkylating or cross-linking agents, toxins, and anti-microbial agents, such as polyene antibiotics (exemplified by amphotericin B). Finally, a combination of compounds may be used. This list of examples is in no way intended to be exhaustive nor meant to limit the scope of this invention. Many other effector molecules may be suitable for the purposes of the present invention. An advantage of the pre-targeting concept with therapeutic radionuclides is that longer lived isotopes may have a therapeutic advantage. In the future, radionuclides previously considered too long lived for radioimmunotherapy may be preferred (e.g., $^{225}$Ac, $^{32}$P).

Linkage of Enzyme Inhibitor to Effector Molecule

The methods by which enzyme inhibitors and diagnostic or therapeutic agents may be derivatized and covalently coupled are numerous and well known in the art. For example, enzyme inhibitors containing nucleophilic moieties such as primary amine, a thiol, or a hydroxyl group may be reacted with effector molecules that contain electrophilic moieties or have been derivatized with such a moiety. Examples of electrophilic moieties include alkyl halides, alkyl sulfonates, active esters such as N-hydroxysuccinimide esters, aldehydes, ketones, and other electrophilic moieties such as isothiocyano, maleimido, or carboxylic acid chloride residues. Vice versa, effector molecules containing a nucleophilic moiety can be reacted with an electrophilic moiety on the enzyme inhibitor molecule. Thus, any of a wide range of functional groups on both the enzyme inhibitor and the effector molecule may be utilized for conjugation, provided these groups are complementary. Alternatively, effector molecules may be coupled to enzyme inhibitors using hetero- or homobifunctional cross-linking reagents. Suitable reactions would be well known to one skilled in the art based on the nature of the reactive groups that are available or have been introduced to both molecules and information about the active site requirements of the inhibitor and the effector molecule.

Preferred for the coupling of radionuclides to enzyme inhibitors are chelating agents capable of forming a tight metal complex with a variety of pharmaceutically useful metals. Typically, the chelate moiety is coupled to the enzyme inhibitor by reaction with a nucleophilic moiety, such as a primary amino group, or with an electrophilic moiety, such as an active ester.

EXAMPLE I

Figure 1:
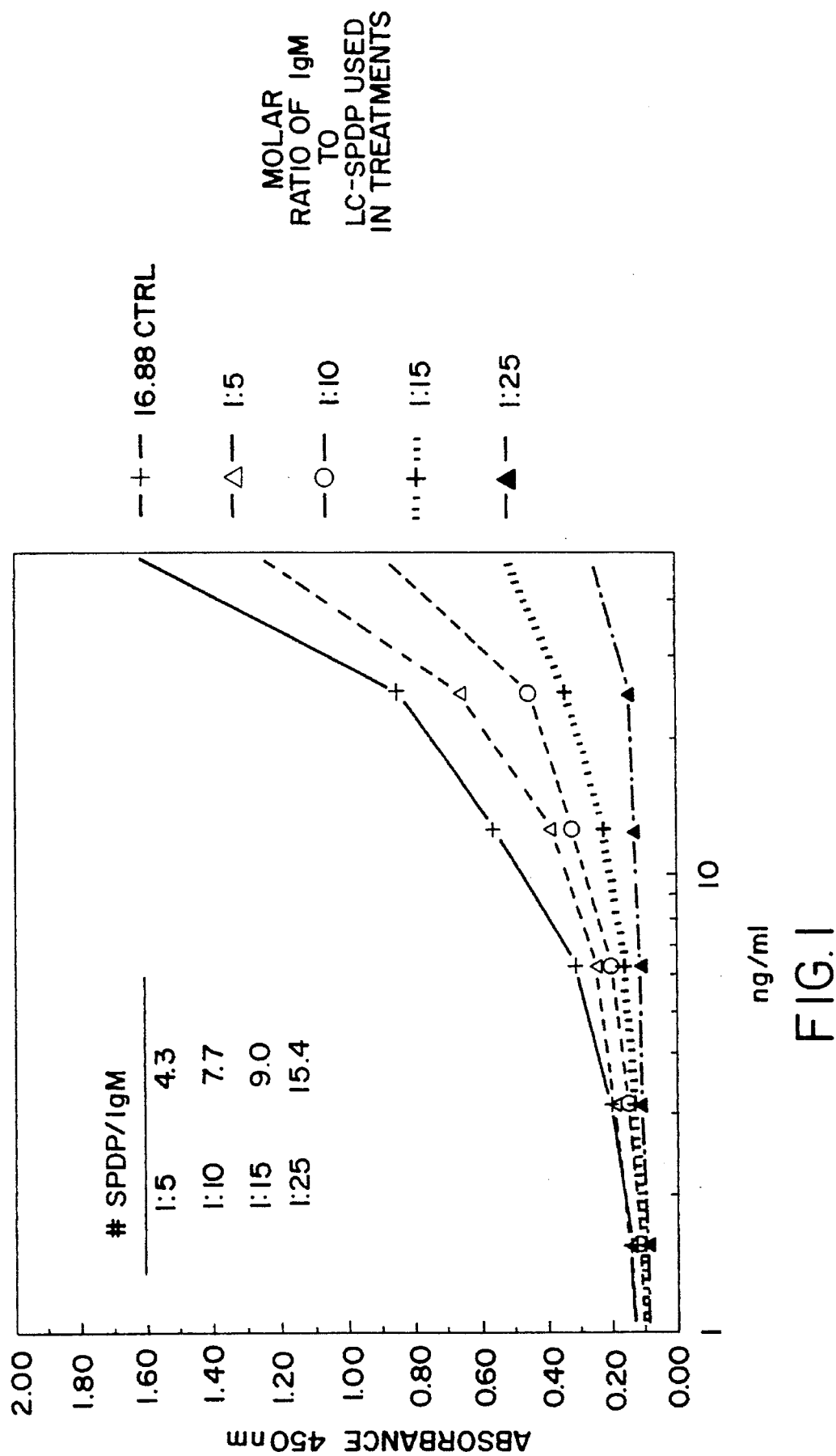
FIG. 1 shows immunoreactivity of the SPDP modified 16.88 which was determined by measuring binding to the tumor antigen CTAA-16.88 and comparing to the activity of native 16.88.

Incorporation of a Spacer with a Terminal Sulfhydryl Group Through Amino Groups on the Antibody Using SPDP SPDP modified 16.88 was prepared by reacting a 15 molar excess of sulfo-LC-SPDP with the antibody in 0.1M phosphate, 0.1M NaCl, pH 7.2 for 30 min. at room temperature with intermittent mixing. A typical reaction contained 5 mg of IgM antibody (6.7 nmoles) and 53 μg of sulfo-LC-SPDP (100 nmoles) in a volume of 2 mL. After derivitization, the SPDP modified antibody was purified on a Sephadex G-25 column equilibrated in 0.1M phosphate, 0.1M NaCl pH 7.2, subsequently concentrated on a Centricon-30, and stored at 4° C. at no less than 2 mg/mL. SPDP incorporation was determined by adding dithiothreitol (DTT) to final concentration of 10mM to an aliquot of the SPDP modified antibody and monitoring the release of 2-pyridylthione at 343 nm. The release of 1 mole of 2-pyridylthione is equivalent to the incorporation of 1 mole of sulfhydryl and can be quantitated with an extinction coefficient of 8,080$M^{-1}$ $cm^{-1}$. Protein concentration was determined using the BCA protein assay and the degree of sulfhydryl incorporation determined. Immunoreactivity of the SPDP modified 16.88 was determined by measuring binding to the tumor antigen CTAA-16.88 and comparing to the activity of native 16.88 (FIG. 1).

EXAMPLE II

Incorporation of a Spacer with a Terminal Sulfhydryl Group Through Amino Groups on Dihydrofolate Reductase Using SPDP SPDP modified recombinant human dihydrofolate reductase (rhDHFR) was prepared by reacting a 10 molar excess of sulfo-LC-SPDP with rhDHFR in 0.1M phosphate, pH 7.5 for 30 minutes at room temperature with intermittent mixing. A typical preparation contained 0.5 mg of rhDHFR (24 nmoles) and 126 μg of sulfo-LC-SPDP (240 nmoles) in a volume of 2 mL. After derivatization, the SPDP modified rhDHFR was purified on a Sephadex G-25 column equilibrated in 0.1M phosphate, 0.1M NaCl, pH 7.2 and concentrated on a Centricon-3. Sulfhydryl incorporation (FIG. 2) and protein concentration determination were performed as described for the antibody. Since rhDHFR contains no disulfide bonds, the SPDP's incorporated onto the enzyme could be deprotected with dithiothreitol (DTT) without detrimental effects to the enzyme. To do this, SPDP-rhDHFR was treated with DTT at a final concentration of 10 mM for 20 min. at room temperature in 0.1M phosphate, 0.1M NaCl 1 mM EDTA pH 7.2, purified on a Sephadex G-25 column equilibrated in degassed 0.1M phosphate, 0.1M NaCl, 1 mM EDTA, pH 7.2., and then concentrated on a Centricon-3. After determining the protein concentration by absorbance at 280 nm, the derivatized rhDHFR was immediately used to prepare the final immunoconjugate. The activity of rhDHFR following sulfo-LC-SPDP modification and following reduction with DTT was evaluated to determine the effects of the treatment on the activity of the enzyme (FIG. 3).

EXAMPLE III

Formation of the Antibody-Enzyme Complex

The immunoconjugate was prepared by adding a 10–15 molar excess of derivatized rhDHFR to 16.88-SPDP. The reaction was performed in a volume of 2.5 mL of 0.1M phosphate, 0.1M NaCl, 1 mM EDTA, pH 7.2 at 4° C. for 3–4 days under $N_2$. One to two mg of 16.88-SPDP (1.3–2.6 nmoles) was used in a typical reaction and the amount or derivatized rhDHFR used determined by the antibody quantity used. After incubation at 4° C., the mixture was concentrated to 1 mL or less and the immunoconjugate purified on a Fractogel 55S column equilibrated in 0.1M phosphate, 0.1M, NaCl, pH 7.2. The immunoconjugate was concentrated on a Centriprep-30 membrane and stored at 4° C. The immunoreactivity and protein concentration were determined as described earlier. FIG. 4 shows the immunoreactivity of two preparations of 16.88-DHFR. FIGS. 5 and 6 show the beneficial effects of using the LC-SPDP spacer compared to normal SPDP in three different conjugate preparations. In all cases, the number of active DHFR's on the IgM was improved by using LC-SPDP.

EXAMPLE IV

Assay of Dihydrofolate Reductase Activity

Dihydrofolate reductase concentrations of $10^{-7}$–$10^{-9}$M are easily assayed by monitoring the time dependent decrease in $A_{340}$ caused by the reduction of dihydrofolate and the oxidation of the cofactor nicotinadenine dinucleotide phosphate (NADPH). The assay is performed at 22° C. (room temperature) in 50 mM Tris, pH 7.5 and 60 µM NADPH and initiated by adding dihydrofolate to 50 µM. One enzyme unit is equivalent to the amount of enzyme required to reduce 1 µmole of dihydrofolate to 1 µmole tetrahydrofolate in 1 min. at 22° C. and can be quantitiated using an extinction coefficient of 12,300$M^{-1}$ $cm^{-1}$.

The inhibition rate of DHFR by MTX and its derivatives is determined by the decrease in the conversion of dihydrofolate to tetrahydrofolate. The assay conditions are identical to the assay conditions above with only the addition of methotrexate or its derivatives at [MTX]≦[DHFR]. Derivatives of methotrexate are evaluated by comparing inhibition rates to the inhibition rate of MTX at equivalent concentrations. Inhibition constants ($K_i$) for MTX and its derivatives can be determined by plotting 1/V (v=velocity (µmole)) vs 1/[S]([S]=substrate concentration, i.e., DHF) at different inhibitor concentrations, determining $$Km_{app}\left(Km_{app} = \frac{1}{x - \text{intercept}}\right),$$

and using the equation $$-\frac{1}{Km_{app}} = -\frac{1}{K_i + \left(1 + \frac{[I]}{K_i}\right)}$$

to solve for $K_i$; ($Km = Km_{app}$ at [I]=O.

EXAMPLE V

Assay of the Inhibitory Activity of Methotrexate-DTPA on Dihydrofolate Reductase The effects of modifying methotrexate with DPTA were unknown and required a comparison of the activity of equimolar concentrations of methotrexate and DTPA-MTX. Since the opterin ring had not been modified and no additional chromophores had been placed on methotrexate during DTPA modification, the extinction coefficient of MTX (E=22,100$M^{-1}$ $cm^{-1}$ at 302 nm)) was used to determine the concentration of DTPA-MTX. The inhibition of rhDHFR by MTX and DTPA-MTX were then measured under the assay conditions mentioned earlier and compared. FIG. 7 shows that at $1\times10^{-8}$M and $5\times10^{-9}$M inhibitor concentration, the inhibitory effects of DTPA-MTX were virtually identical to MTX inhibition; as indicated by the decreased rates of dihydrofolate reduction.

EXAMPLE VI

Analysis of the Inhibitory Activity of MTX and DTPA-MTX on DHFR Bound in an Antibody DHFR Complex As shown earlier, 16.88-DHFR conjugates have been prepared which possessed easily assayable quantities of rhDHFR. Although the reductase activity was measurable, there was no guarantee that the MTX binding properties of the conjugated enzyme had not been affected during the modification steps. To confirm that MTX binding was proportional to the dihydrofolate reductase activity in 16.88-DHFR, the DHFR activity in the conjugate was titrated to an equivalent amount of native rhDHFR and these activity equivalents were compared for their ability to be inhibited by MTX and DTPA-MTX. FIG. 8 shows the results of MTX inhibition of equivalent activities of native rhDHFR and 16.88 bound rhDHFR and indicates that MTX binding is proportional to the reductase activities regardless of whether it is free or in conjugate form. An identical experiment performed using DTPA-MTX (FIG. 9) confirmed the methotrexate data. From these results, not only has the reductase activity been maintained in the conjugate, but also the ability of MTX and DTPA-MTX to bind to and inhibit the conjugated rhDHFR.

EXAMPLE VII

Synthesis of DTPA-MTX

Much effort has been devoted toward potent folate analogues and it is well known that the glutamate moiety contributes to the binding of MTX to dihydrofolate reductase while the γ-carboxyl does not. We have designed MTX analogues that contain a chelator molecule at the γ-carboxyl group of the glutamic acid portion.

The synthesis of DTPA-MTX is shown schematically in FIG. 10. The MTX-AB-GH was prepared using the general method of Rosowsky et al., J. Med. Chem., 1981, 24, 1450–1455. The DTPA dianhydride (9.3 mg, 25 µmol) was dissolved in DMF and stirred with $Et_3N$ (0.1 mL) for 5 min. MTX-AB-GH 6.8 mg (13 µmol) in 2 mL of $CH_3CN$ was added to the above mixture and stirred overnight at room temperature. Solvents were evaporated and the residue was heated to 50° C. with 1N HCl for 1 hour. The reaction mixture was evaporated to dryness and the residue was purified by HPLC (a $C_{18}$, reversed-phase silica gel column, absorbance at 280 nm, the mobile phase was formed with 2% acetic acid (pump A) and 2% acetic acid in 50% methanol (pump B); $t_R$=17.56 min (cf. $t_R$ of MTX=25.26 min) to give 4.1 mg (38%) of product; FAB-MS m/z=844 $(M+H)^+$; $^1H$ NMR ($D_2O$) δ 8.49 (s,1H), δ 7.52 (d,J=8.6 Hz, 2H) δ 6.72 (d, j=8.6 Hz, 2H), δ 4.4 (m, 1H), δ 3.0–3.95 (m, 18H) δ 3.7 (s, 2H), δ 3.1 (s, 3H), δ 2.39 (t, 2H), δ 1.9–2.3 (m, 2H).

EXAMPLE VIII

Clearance of $^{111}$In-DTPA-MTX from Athymic Mice Radiolabeling DTPA-MTX with In-111

$^{111}$InCl$_3$ (1.5 mCi) is mixed with 0.06 mL (0.6 mg) DTPA-MTX, 0.02 mL 0.06 sodium citrate pH 5.5, and 0.01 mL 0.60 sodium acetate pH 5.5 for 30 minutes to 215 minutes at room temperature. Thin layer chromatography on plastic backed silica gel strips (1.1 ammonium acetate:methanol) using 0.001 mL of the final reaction solution showed greater than 95% incorporation of $^{111}$In into the $^{111}$In-DTPA-MTX complex. FIG. 11 shows the migration of $^{111}$In-DTFA-MTX in the silica gel with an R$_f$ of 0.5 to 0.7. Free $^{111}$In does not migrate from the origin in this system.

This example compares the whole body clearance of $^{111}$In-DTPA-MTX with that of $^{111}$In-DTPA. $^{111}$In-DTPA is known to clear rapidly from the circulation with little retention in normal tissues. Clearance of the $^{111}$In-DTPA-MTX at a rate similar to that of $^{111}$In-DTPA would indicate that rapid body clearance of the portion of the conjugate not bound in tumor tissue by antibody-DHFR may be expected. Such rapid clearance would ensure that nearly all the unbound radionuclide would decay outside the body.

Three athymic nu/nu mice were injected via the lateral tail vein with 50 uCi $^{111}$In-DTPA-MTX in 0.5 mL 10% normal mouse serum in phosphate buffered normal saline. A second group of three animals received 50 uCi $^{111}$In-DTPA by the same route. All animal were examined for whole body retention of In-111 in a Capintec dose calibrator at 0.5, 1, 2, 3, 4, and 24 hours after injection.

Results shown in FIG. 12 indicate that the $^{111}$In-DTPA-MTX and the $^{111}$In-DTPA clear from the mice at similar rates indicating the likelihood of rapid urinary excretion of a DTPA-MTX not bound to antibody-DHFR.

EXAMPLE IX

Binding of $^{111}$In-DTPA-MTX to Tumor Cell-Bound Antibody-DHFR

This example examines the targeting of $^{111}$In-DTPA-MTX to antibody-DHFR bound to K562 cultured erythroleukemia cells in vitro. For this demonstration, DHFR was coupled to the murine antibody to the human transferrin receptor (5E9C11) using the methods described in example 1. This antibody rather than the human anti-colon carcinoma antibody 16.88 was used since an antibody that binds to epitopes on the surface of cultured cells was required for this in vitro demonstration.

In the first study binding of antibody-DHFR to the target cells was assessed in a titration using concentrations of antibody-DHFR of 1.5, 3.0, 6.0, 12.0, and 24.0 ug/mL mixed at 4° C. with 1×10$^6$ K562 cells in a medium consisting of Hanks Balanced Salt Solution containing 1% bovine serum albumin (protease-free). The reaction volume was 0.2 mL reacted for 60 minutes in an ice bath to prevent internalization of the antibody bound to the transferrin receptor. After washing away excess antibody, 10 ng $^{111}$In-DTPA-MTX (0.53 uCi) was added and the reaction continued for 30 minutes in an ice bath.

Results of the titration are shown in FIG. 13. Non-specific binding of the $^{111}$In-DTPA-MTX, determined with antibody to which no DHFR was conjugated, averaged 0.85% at all antibody concentrations. The study demonstrated that $^{111}$In-DTPA-MTX can bind to antibody-DHFR bound to tumor cells. The extent of binding was sufficient to saturate all available DHFR sites as determined from estimates of the amount of DHFR bound to the cells and the specific activity of the $^{111}$In-DTPA-MTX. As no plateau level was reached it is apparent that at an antibody-DHFR concentration of 24 ug/mL the available binding sites on the tumor cells were not saturated in this study.

In the second study, the lowest concentration of antibody-DHFR giving significant binding above the background level (6.0 ug/mL) was used in a titration of the $^{111}$In-DTPA-MTX using concentrations of 12.5, 25, 50, 100, or 200 ng/mL (0.31 to 3.7 uCi/mL) with conditions identical to those described for the first study. Results are shown in FIG. 14. Again binding of $^{111}$In-DTPA-MTX to cell-bound antibody-DHFR was demonstrated. At concentrations above 50 ng/mL, binding reached a plateau level indicating saturation of the available DHFR binding sites, in agreement with the conclusions of the first study.

EXAMPLE X

Stabilization of Dihydrofolate Reductase (rhDHFR)

In our most preferred embodiment we use stabilized rhDHFR (Dr. James Freisbeim, Medical College of Ohio, Toledo, Ohio) as the enzyme. DHFR was stabilized through covalent conjugation of the enzyme with a photoaffinity analog of NADP$^+$ (ANPAP-NADP) followed by photoactivation using a tungsten halogen lamp (615 W; DVY; 3400° K.).

A 10-fold molar excess of the photoaffinity analog was mixed with the enzyme, and the volume adjusted to a protein concentration of 1 mg/ml using 10 mM Tris-HCl buffer (pH 7.5). The mixture was kept in ice at a 10 cm distance from the light source while photoactivation was carried out for 5 minutes with occasional stirring. An aliquot was assayed for DHFR activity before and after photoactivation. The NADP$^+$-linked enzyme was purified by gel-filtration using 10 mM sodium phosphate buffer, pH 7.2, containing 20 mM NaCl. Fractions were assayed for DHFR activity before they were pooled for protein estimation (using Pierce BCA reagent) and determination of incorporation of NADP$^+$ moieties per enzyme molecule.

Stability of the conjugated enzyme was determined by incubating at 37° C. for several hours. Percent stability was calculated by comparing with a sample kept at 4° C.

Results

Conjugation
Photoactivation Time: 5 minutes
Percent remaining activity following photoactivation: 100%
Number moieties per enzyme molecule 2.21:1

Stability

| Sample | Time (minutes) | | | | | |
| --- | --- | --- | --- | --- | --- | --- |
|  | 0 | 30 | 60 | 120 | 180 | 1080 |
| ANPAP-NADP$^+$-rhDHFR | 100[1]% | N.T.[2] | 82[1]* | 78[1]% | 78[1]% | 67[3]% |
| rhDHFR | 100[1]% | 18[1]% | 10[1]% | N.T. | N.T. | N.T. |

[1]Values represent percent enzyme activity remaining after incubation at 37° C.
[2]N.T. - Not Tested.
[3]Values represent percent enzyme activity remaining after incubation at 23° C.

Synthesis of the stabilizer of N3'-O-[3-(4-azido-2nitrophenyl)amino]propionyl NADP+ (ANPAP-NADP)

A modified procedure of the Chen and Guillory's method (Chen, S. and Guillory, R. J., J. Biol. Chem., 1980, 255, 2445–2453) was used and the detailed procedure was as follows: A dimethyl formamide (DMF) solution of carbodiimidazole (CDI) (324 mg, 2 mmol) and 3-(4-azido-2-nitrophenylamino) propionic acid (Jeng, S. J. and Guillory, R. J., J. Supramolecular Structure, 1975, 3, 445–468) (15 mg, 0.6 mmol) was stirred at room temperature for 15 min. Then about 3 ml aqueous solution of NADP+ (64.6 mg, 0.08 mmol) was added to the DMF solution. Stirring was continued overnight under a nitrogen atmosphere. The solvent was then removed by a rotary evaporator and the residue was washed with acetone by centrifugation. The residue was then dissolved in a small amount of water and purified by preparative thin layer chromatography (Taper® plate; solvent system: 1-butanol/water/HOAc=5/3/2). The material ($R_F$=0.4) was recovered. The compound was further purified by HPLC (Reverse Phase $C_{18}$ column UV @ 260 nm).

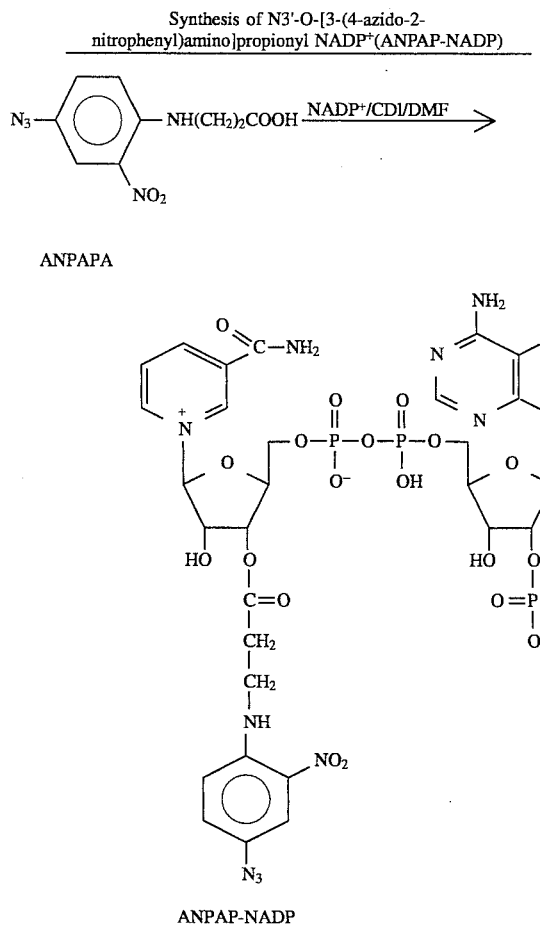

Synthesis of N3'-O-[3-(4-azido-2-nitrophenyl)amino]propionyl NADP+(ANPAP-NADP)

ANPAPA

ANPAP-NADP

We claim:

1. A method for the in vivo targeting of an effector molecule in a patient comprising:
   first administering a targeting moiety coupled to an enzyme to form a targeting moiety-enzyme conjugate, wherein said targeting moiety is selected from the group consisting of an antibody, an antibody fragment, an antibody variable region, a complimentarity determining region of an antibody, a bivalent antibody, a hybrid antibody and a chimeric antibody, and thereafter administering a binding partner for the enzyme, wherein the binding partner is an enzyme inhibitor, coupled to an effector molecule forming an effector complex, whereby said effector complex through the binding partner binds to the enzyme to localize said effector molecule in the target area.

2. The method of claim 1, wherein the enzyme is an intact enzyme, a fragment of an enzyme, a derivative of an enzyme comprising the inhibitor binding region of an enzyme or a molecule that mimics the inhibitor binding region of an enzyme.

3. The method of claim 1, wherein the effector molecule is a pharmacologically active compound.

4. The method of claim 1, wherein the effector molecule is a radionuclide or a toxin.

5. The method of claim 4, wherein the effector molecule is a radiometal.

6. The method of claim 1, wherein the enzyme inhibitor is methotrexate and the effector molecule comprises a radiometal.

7. The method of claim 1, wherein the enzyme is stabilized dihydrofolate reductase.

8. The method of claim 1, wherein the effector complex comprises a binding partner which is coupled to an effector molecule by way of a cross-linking molecule that has one or more functional moieties that can bind to the effector molecule.

9. The method of claim 8, wherein the cross-linking agent is a homo- or hetero-bifunctional cross-linking reagent.

10. The method of claim 8, wherein the cross-linking agent is a chelating moiety.

11. The method of claim 10, wherein the effector complex comprises methotrexate as the enzyme inhibitor, the cross-linker is a hydrazide derivative of diethylenetriaminepentaacetic acid (DTPA) and the effector molecule is a radiometal that is chelated to the DTPA.

* * * * *